United States Patent [19]

Fuseya et al.

[11] 4,191,576
[45] Mar. 4, 1980

[54] LIGHT-SENSITIVE SILVER HALIDE PHOTOGRAPHIC ELEMENT CONTAINING UV ABSORBER

[75] Inventors: Yoshiharu Fuseya; Atsuo Inoue; Hiroshi Hara; Tadashi Ikeda, all of Minami-ashigara, Japan

[73] Assignee: Fuji Photo Film Co., Ltd., Minami-ashigara, Japan

[21] Appl. No.: 900,376

[22] Filed: Apr. 26, 1978

[30] Foreign Application Priority Data

Apr. 27, 1977 [JP] Japan ................... 52-48953

[51] Int. Cl.$^2$ .............................................. G03C 1/84
[52] U.S. Cl. ........................... 430/512 V; 430/517; 430/613; 430/614
[58] Field of Search ............... 96/84 R, 84 UV, 95, 96/120, 87 R

[56] References Cited

U.S. PATENT DOCUMENTS

| 3,486,897 | 12/1969 | Oliver | 96/84 R |
|---|---|---|---|
| 3,629,274 | 12/1971 | Oliver | 96/120 |
| 3,652,284 | 3/1972 | Oliver | 96/84 R |
| 3,770,757 | 11/1973 | Oliver | 96/84 R |

*Primary Examiner*—Jack P. Brammer
*Attorney, Agent, or Firm*—Sughrue, Rothwell, Mion, Zinn and Macpeak

[57] ABSTRACT

A light-sensitive silver halide photographic material comprising a support having thereon at least one light-sensitive silver halide emulsion layer, with the silver halide photographic material containing at least one compound represented by the following general formula (I):

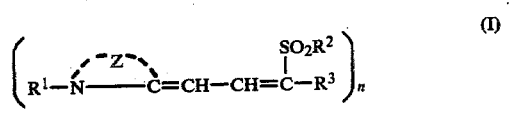

wherein Z represents the atoms necessary to complete an oxazolidine ring, a pyrrolidine ring or a thiazolidine ring; $R^1$ and $R^2$, which may be the same or different, each represents an alkyl group or an aryl group; $R^3$ represents a —$COR^4$ group or a —$CO_2R^5$ group; $R^4$ represents an alkyl group or an aryl group; $R^5$ represents a hydrogen atom, an alkyl group or an aryl group; and n is 1 or 2, at least one of $R^1$, $R^4$ and $R^5$ represents a divalent alkylene group, a divalent arylene group or a divalent group of alkylene and arylene moieties to form a dimer; and a method for preventing the effects of ultraviolet light on a silver halide photographic material comprising incorporating, as an ultraviolet light absorbent, at least one compound represented by the general formula (I) above into the silver halide photographic material.

40 Claims, No Drawings

LIGHT-SENSITIVE SILVER HALIDE PHOTOGRAPHIC ELEMENT CONTAINING UV ABSORBER

BACKGROUND OF THE INVENTION

1. Field of the Invention

The present invention relates to a light-sensitive silver halide black-and-white photographic or color photographic material, and, particularly, to a light-sensitive silver halide color photographic material in which the deleterious influence of ultraviolet light is obviated by incorporating an ultraviolet light absorbing agent therein.

2. Description of the Prior Art

It is well known that ultraviolet light deleteriously influences a photographic light-sensitive material. A photographic light-sensitive material comprises a support having a comparatively high electric insulation property such as a film support of cellulose triacetate, polyethylene terephthalate, polystyrene or polycarbonate and a laminated paper covered with any of these polymers, and a light-sensitive photographic emulsion layer, which contains silver halide as a primary component, coated onto the support. Both surfaces of a photographic light-sensitive material have, therefore, a remarkably high electric insulation property. Accordingly, an electric charge is generated when the surface of the photographic light-sensitive material contacts another photographic light-sensitive material or different material and subsequently is rubbed therewith or separated therefrom during production or handling of the photographic light-sensitive material. This phenomenon is called "electrification". Once the accumulated static electricity reaches a limit, an atmospheric electric discharge occurs and a spark is formed at the same time due to the electric discharge. Since a photographic light-sensitive material is sensitive to light due to the spark discharge, an arborescent image, a feather-like image, a dot image or a radiated image is formed on the photographic material following development processing. The images thus-formed are called "static marks" in the photographic art. It is known that the spectral energy distribution of light due to spark discharge which causes static marks ranges from about 200 nm to about 550 nm and the intensity of light particularly with wavelengths of about 300 nm to about 400 nm is sufficiently high that the energy of light in this wavelength region causes the appearance of static marks. Accordingly, methods to prevent the appearance of static marks which comprise shielding from ultraviolet light particularly with wavelengths of about 300 nm to about 400 nm by utilizing an ultraviolet light absorbing agent have been hitherto investigated, as described in, for example, Japanese Patent Publication 10726/1975, Japanese Patent Application (OPI) 26021/1976 (The term "OPI" as used herein refers to a "published unexamined Japanese patent application") and French Pat. No. 2,036,679.

Other than certain photographic light-sensitive materials which are designed for exposure to light from special light-sources such as photosensitive materials for the graphic arts and X-ray photosensitive materials, exposure of a conventional photographic light-sensitive material to a light source containing ultraviolet light sometimes gives rise to undesirable effects. For example, light reflected from a snowscape, the beach and the sky has such a high spectral energy in the ultraviolet light region that the image reproduced in a black-and-white photographic light-sensitive material tends to have low contrast. This phenomenon is more markedly observed in a color photographic light-sensitive material in which a silver halide photographic emulsion layer is sensitized to light with wavelengths longer than the wavelength region to which silver halide is intrinsically sensitive and in which recording only visible light is desired.

Further, when light having a comparatively high spectral energy in the ultraviolet light region such as light reflected from a distant view, a snow covered landscape and an asphalt pavement is photographed, a bluish color image is obtained. In addition, the quality of the color reproduction of the finished color image varies considerably based on the difference in spectral energies in the ultraviolet light region of light from various types of light sources used for exposure, such as sunlight, a tungsten lamp and a fluorescent lamp. That is, the color images obtained upon exposure to light from a tungsten lamp and from a fluorescent lamp have a reddish color tone and a bluish color tone, respectively, as compared to the color tone obtained upon exposure to sunlight. Accordingly, in order to obtain a color photograph with the correct color reproduction, it is desirable for the silver halide photographic emulsion layer of a color photographic light-sensitive material to not be exposed to ultraviolet light, for example, as described in Japanese Patent Application (OPI) No. 56620/1976 corresponding to U.S. Pat. No. 4,045,229.

Furthermore, a color photograph, particularly a color photograph of the type where a dye image is formed in a light-sensitive photographic emulsion layer by color development tends to fade and to discolor due to the action of ultraviolet light. In addition, a coloring agent which remains in a photographic emulsion layer after the formation of the color image forms an undesirable color stain on the finished color image due to the action of ultraviolet light. This type of effect due to ultraviolet light on a finished color image is particularly marked in a positive print which is often viewed under sunlight containing a large amount of ultraviolet light. The dye image tends to fade and to discolor particularly due to the action of ultraviolet light having a spectral energy in the wavelength region near the visible region, i.e., of about 300 nm to about 400 nm. Many methods of utilizing an ultraviolet light absorbing agent in order to minimize the deleterious effect of ultraviolet light have been made as described in, for example, U.S. Pat. Nos. 3,215,530, 3,707,375, 3,705,805, 3,352,681, 3,278,448, 3,253,921 and 3,738,837, Japanese Patent Publications 26138/1974 and 25337/1975, U.S. Pat. No. 4,045,229 and British Pat. No. 1,338,265.

Generally, photographic ultraviolet light absorbing agents must have the following properties:

(1) The ultraviolet light absorbing agents themselves must be colorless or substantially colorless;
(2) They must have a good compatibility with a binder;
(3) They must be inert to other photographic additives and elements present;
(4) They must have good ultraviolet absorption characteristics, i.e., they must effectively absorb ultraviolet light having wavelengths of about 300 nm to about 400 nm; and
(5) They must be stable to ultraviolet light, heat and moisture.

Ultraviolet light absorbing agents which have heretofore been used do not have sufficiently desirable characteristics and do not have the above-described properties. For example, the benzotriazoles as described in, for example, U.S. Pat. No. 3,253,921 and the cinnamic acid type compounds as described in, for example, U.S. Pat. Nos. 3,707,375 and 3,705,805 have been generally used in photographic light-sensitive materials for a long time. However, they have inferior light absorption characteristics in the wavelength region of from about 300 nm to about 400 nm, and have a low coefficient of light absorption particularly in the wavelength region of from about 360 nm to about 395 nm. (These wavelengths are those absorption wavelengths determined in a hydrophilic colloid aqueous solution, hereinafter the same.) Additionally, prior art ultraviolet absorbing agents have broad absorption spectral curves. Therefore, a large amount of the prior art ultraviolet absorbing agent must be added to a photographic light-sensitive material in order to obtain a desired absorption density. However, when these ultraviolet light absorbing agents are utilized in sufficient amount to provide a desired absorption density particularly in the wavelength region of from about 360 nm to about 395 nm, visible light having wavelengths longer than about 415 nm is also absorbed to a substantial extent by these ultraviolet absorbing agents. This results in both a reduction in sensitivity due to the filtering action and a formation of an undesirable stain. Accordingly, these ultraviolet light absorbing agents cannot be employed in a sufficiently large amount that a desirable absorption density can be obtained in the wavelength region of from about 360 nm to about 395 nm. As a consequence, the absorption of ultraviolet light with these prior art ultraviolet absorbing agents is not sufficiently effective that prevention of static marks and improvement in both color reproduction and color image stabilization can be obtained. In addition, the use of an ultraviolet light absorbing agent in a large amount tends to cause difficulties, e.g., poor contact between layers of a multilayer photographic light-sensitive material and adhesion between photographic light-sensitive materials.

SUMMARY OF THE INVENTION

An object of the present invention is to provide a light-sensitive silver halide photographic material having improved color reproduction characteristics and where both the generation of static marks and light fading and light discoloration of the dye image formed are minimized by utilizing an ultraviolet light absorbing agent.

Another object of the present invention is to provide a light-sensitive silver halide photographic material containing an ultraviolet light absorbing agent, in which the above-described disadvantages have been obviated without deleteriously influencing, for example, photographic properties such as sensitivity and fog and physical properties such as adhesion.

Another object of the present invention is to provide a method of minimizing the effect of ultraviolet light, particularly, ultraviolet light having wavelengths of about 360 nm to about 395 nm on the silver halide and/or an image of a photographic light-sensitive material.

As a result of various investigations, it has now been found that ultraviolet light can be effectively absorbed and additionally the above-described objects of the present invention can be effectively attained in one embodiment of this invention providing a silver halide photographic material comprising a support having thereon at least one light-sensitive silver halide emulsion layer, with the photographic material containing, as an ultraviolet light absorbing agent, at least one compound represented by the general formula (I):

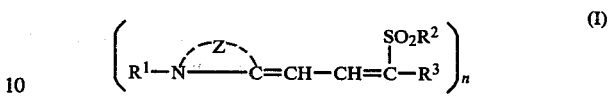

wherein Z represents the atoms necessary to complete an oxazolidine ring, a pyrrolidine ring or a thiazolidine ring; $R^1$ and $R^2$, which may be the same or different, each represents an alkyl group or an aryl group; $R^3$ represents a —$COR^4$ group or a —$COOR^5$ group; $R^4$ represents an alkyl group or an aryl group; $R^5$ represents a hydrogen atom, an alkyl group or an aryl group; n is 1 or 2, and when n is 2, at least one of $R^1$, $R^4$ and $R^5$ represents a divalent alkylene group, a divalent arylene group or a divalent group of alkylene and arylene moieties to form a dimer.

The above-described objects are also achieved in another embodiment of this invention which provides a method for preventing the effects of ultraviolet light on a silver halide photographic material comprising a support having thereon at least one light-sensitive silver halide emulsion layer by incorporating, as an ultraviolet light-absorbing agent, at least one compound represented by the general formula (I) above into the photographic material.

It is particularly preferred for the compound represented by the general formula (I) to be incorporated in the form of an emulsified dispersion.

DETAILED DESCRIPTION OF THE INVENTION

In the general formula (I) above, the oxazolidine ring, the pyrrolidine ring and the thiazolidine ring completed by Z can be unsubstituted or can be substituted with one or more substituents. Examples of suitable substituents include an alkyl group having up to about 10 total carbon atoms (which may be unsubstituted or substituted with one or more of a hydroxy group, an alkoxy group having 1 to 4 carbon atoms, e.g., a methoxy group, an ethoxy group, a propoxy group, a butoxy group, etc., an aryl group having 6 to 12 carbon atoms, e.g., a phenyl group, a tolyl group, a p-tert-butylphenyl group, a p-chlorophenyl group, an anisyl group, etc., a carboxy group, a halogen atom, e.g., a chlorine atom, a bromine atom, a fluorine atom, etc., an alkoxycarbonyl group having 2 to 6 carbon atoms, e.g., a methoxycarbonyl group, an ethoxycarbonyl group, a butoxycarbonyl group, etc., a dialkylamino group having 2 to 20 total carbon atoms, e.g., a dimethylamino group, a diethylamino group, etc., a cyano group, an aryloxy group having 6 to 12 carbon atoms, e.g., a phenoxy group, a p-methylphenoxy group, a p-tert-butylphenoxy group, a p-methoxyphenoxy group, etc., or the like) and an aryl group having about 6 to 20 total carbon atoms (which may be unsubstituted or substituted with one or more of an alkyl group having 1 to 5 carbon atoms, e.g., a methyl group, an ethyl group, a t-butyl group, a t-amyl group, etc., an alkoxy group preferably having 1 to 4 carbon atoms, e.g., a methoxy group, an ethoxy group, a butoxy group, etc., a halogen atom, e.g., a chlorine atom, a bromine atom, etc., a hydroxy group, etc.). Specific examples of suitable heterocyclic rings formed by Z include oxazolidine, 5-methyloxazolidine, 5,5-dimethyloxazolidine, 4-methyloxazolidine, 4,5-dimethyloxazolidine, 5-carboxymethyloxazolidine, 5-phenethyloxazolidine, 5-phenyloxazolidine, pyrrolidine, 5-phenylpyrrolidine, 4-methylpyrrolidine, thiazolidine, 5-methylthiazolidine, 4-methylthiazolidine, 4,5-dimethylthiazolidine, 4-phenylthiazolidine, 5-tolylthiazolidine and 5-phenethylthiazolidine.

Suitable alkyl groups for $R^1$, $R^2$, $R^4$ and $R^5$ include straight chain, branched chain or cyclic alkyl groups and substituted alkyl groups wherein the substituent includes an alkenyl group such as a vinyl group or the like, with preferred examples being alkyl groups having up to about 20 total carbon atoms. Specific examples of alkyl groups for $R^1$, $R^2$, $R^4$ and $R^5$ are unsubstituted alkyl groups and alkyl groups substituted with one or more of a hydroxy group, a halogen atom, e.g., a fluorine atom, a chlorine atom, a bromine atom, etc., an aryl group having 6 to 12 carbon atoms, e.g., a phenyl group, a tolyl group, a p-tert-butylphenyl group, a p-chlorophenyl group, an anisyl group, etc., an alkoxycarbonyl group having 2 to 18 total carbon atoms in the alkyl moiety, e.g., a methoxycarbonyl group, an ethoxycarbonyl group, a dodecyloxycarbonyl group, etc., an alkoxy group having 1 to 16 carbon atoms, e.g., a methoxy group, an ethoxy group, a butoxy group, a 2-ethoxyethoxy group, etc., an alkylcarbonyl group having 2 to 16 total carbon atoms, e.g., an acetyl group, a propionyl group, etc., an arylcarbonyl group having 7 to 16 total carbon atoms, e.g., a benzoyl group, etc., an alkylcarbonyloxy group having 2 to 16 total carbon atoms, e.g., an acetoxy group, a pivaloyloxy group, etc., an arylcarbonyloxy group having 7 to 16 total carbon atoms, e.g., a benzoyloxy group, etc., a cyano group, an alkylsulfonyl group having 1 to 12 carbon atoms, e.g., a methylsulfonyl group, an ethylsulfonyl group, etc., a morpholinocarbonyl group, a carbamoyl group, an N,N-dialkylcarbamoyl group having 2 to 20 total carbon atoms in the alkyl moieties, e.g., an N,N-diethylcarbamoyl group, an N,N-dibutylcarbamoyl group, etc., an N-alkyl-N-arylcarbamoyl group having 7 to 20 total carbon atoms, e.g., an N-methyl-N-phenylcarbamoyl group, an N-butyl-N-phenylcarbamoyl group, etc., an N-alkylcarbamoyl group having 2 to 16 total carbon atoms, e.g., an N-ethylcarbamoyl group, an N-hexylcarbamoyl group, an N-cyclohexylcarbamoyl group, etc., an N,N-dialkylamino group having 2 to 16 total carbon atoms, e.g., an N,N-dimethylamino group, an N,N-diethylamino group, an N-methyl-N-butylamino group, etc., an aryloxy group having 6 to 12 carbon atoms, e.g., a phenoxy group, a 2,4-di-tert-amylphenoxy group, etc., a vinyl group and the like. Representative specific examples include a methyl group, an ethyl group, a butyl group, a hexyl group, a decyl group, an octadecyl group, a dodecyl group, a cyclohexyl group, a β-cyclohexylethyl group, a 2-ethylhexyl group, a hydroxyethyl group, a trifluoroethyl group, a perfluorohexyl group, a benzyl group, a phenethyl group, a p-methylphenethyl group, a methoxycarbonylethyl group, an ethoxycarbonylethyl group, an ethoxyethyl group, a 2-[2-(2-ethoxy)ethoxy]ethyl group, an acetylethyl group, a methylsulfonylethyl group, a cyanoethyl group, a carbamoylethyl group, an N,N-diethylcarbamoylethyl group, a morpholinocarbonylethyl group, an N-methylanilinocarbonylpropyl group, an N,N-diethylaminopropyl group, a phenoxyethyl group, a 2,4-di-tert-amylphenoxyethyl group, an allyl group and the like.

Suitable aryl groups for $R^1$, $R^2$, $R^4$ and $R^5$ include aryl groups, preferably monocyclic or bicyclic and having 6 to 20 total carbon atoms which may be unsubstituted or substituted with one or more of, for example, an alkyl group having 1 to 12 carbon atoms, e.g., a methyl group, an ethyl group, a butyl group, a tert-butyl group, etc., an alkoxy group having 1 to 12 carbon atoms, e.g., a methoxy group, an ethoxy group, a butoxy group, etc., a halogen atom, e.g., a fluorine atom, a chlorine atom, a bromine atom, etc., a cyano group, an amino group, an alkylamino group such as an N,N-dialkylamino group, e.g., an N,N-dimethylamino group, an N,N-diethylamino group, etc., a carboxy group or the like. Representative specific examples of aryl groups include a phenyl group, a tolyl group, a xylyl group, an anisyl group, a p-butoxyphenyl group, a p-chlorophenyl group, a p-cyanophenyl group, a p-N,N-dimethylaminophenyl group, a naphthyl group and the like. Representative examples of divalent alkylene groups, divalent arylene groups and divalent groups consisting of alkylene and arylene moieties for $R^1$, $R^4$ and $R^5$ when a dimer is formed include the following groups:

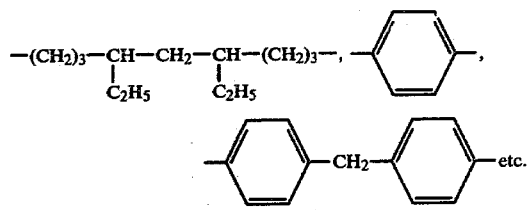

Preferred compounds of the general formula (I) are those where at least one of $R^1$, $R^2$, $R^4$ and $R^5$ is an unsubstituted or substituted alkyl group. In addition, the compound of the general formula (I) preferably is hydrophobic, which can be achieved by utilization of appropriate groups for $R^1$, $R^2$, $R^4$ and $R^5$ and substituents on the Z ring.

Preferred compounds of the general formula (I) are those compounds which are a solid having a melting point of not higher than about 150° C. or which are liquid at room temperature (about 22° to 25° C.). More preferred compounds are those which are a solid having a melting point of not higher than 100° C. or which are liquid at room temperature.

These compounds as specifically mentioned above can be advantageously employed to accomplish the objects of the present invention, since these compounds have good stability (i.e., precipitate in solutions thereof with difficulty) in a hydrophilic colloid aqueous solution and additionally the sharp cut property at about 405 nm of the spectral absorption curve of a hydrophilic colloid aqueous solution containing the compound is excellent.

Generally, there is a difference in the light absorption maximum of an ultraviolet absorbing agent in methanol and in a hydrophilic colloid aqueous solution. That is, where an ultraviolet light absorbing agent is added to a hydrophilic colloid aqueous solution using a "latex dispersion" method, the absorption maximum obtained can shift toward the longer wavelength region by at the most about 5 nm to that in methanol. On the other hand, where an ultraviolet light absorbing agent is dissolved in a substantially water-insoluble high boiling point organic solvent and then the resulting solution is emulsified and dispersed in a hydrophilic colloid aqueous solution, the absorption maximum obtained can shift toward the longer wavelength region by at the most about 30 nm to that in methanol. Thus, an addition method or a dispersion method can be appropriately selected depending on the absorption characteristics of the ultraviolet light absorbing agent.

Typical examples of ultraviolet light absorbing agents represented by the above-described general formula (I) of the present invention are illustrated below. The present invention is not to be construed as being limited to these specific examples, however. The absorption maximum given for each compound was measured as a methanol solution thereof of a concentration of $1\times10^{-5}$ mol/l at a temperature of 25° C.

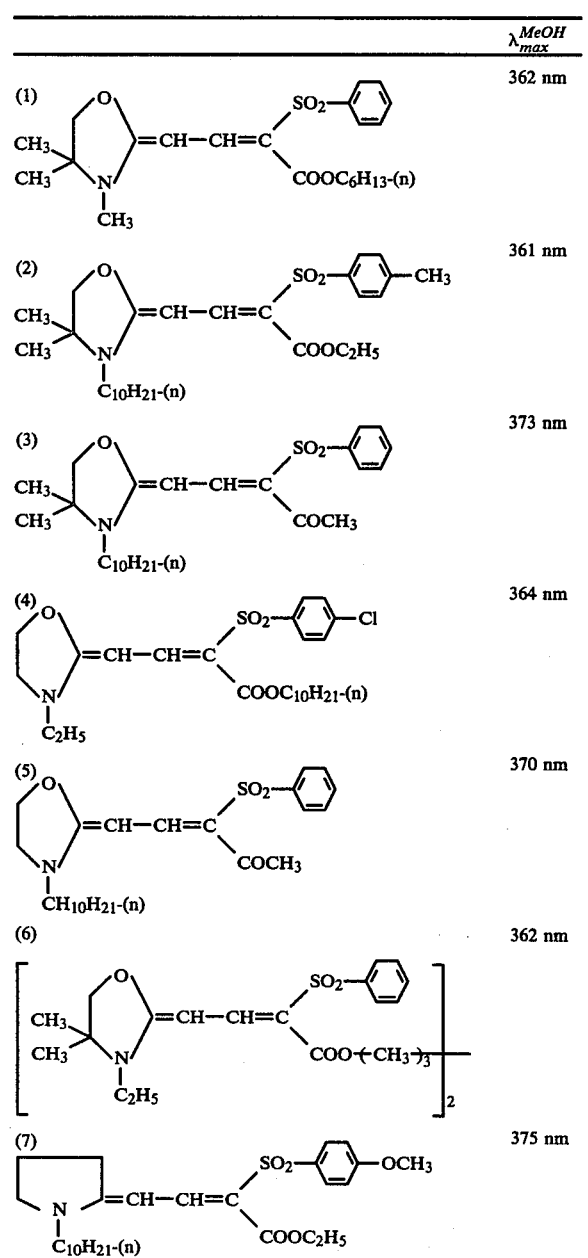
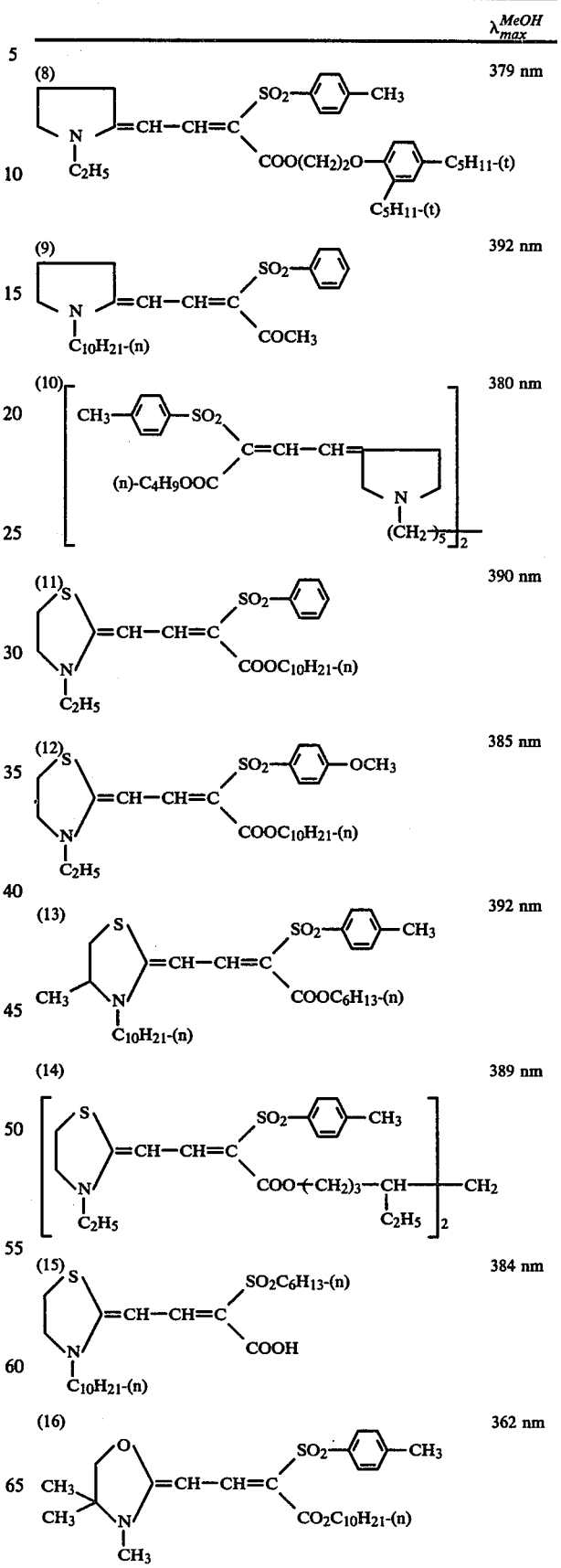

-continued

| | $\lambda_{max}^{MeOH}$ |
|---|---|
| 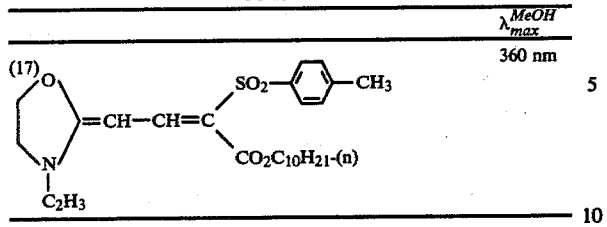 | 360 nm |

Specific examples of the synthesis of typical ultraviolet light absorbing agents according to the present invention are described below. Unless otherwise indicated herein, all parts, percents, ratios and the like are by weight.

SYNTHESIS EXAMPLE 1

Synthesis of Compound (1)

10 ml of triethylamine was added to a mixture of 38 g of 2-(2-N-acetylanilino)vinyl-3,5,5-trimethyloxazolium iodide, 28.9 g of hexyl phenylsulfonylacetate and 200 ml of acetonitrile. The mixture was refluxed with stirring for 30 minutes. The solvent was then removed by distillation under reduced pressure. The residue was chromatographically separated using SiO₂ 60, produced by Merck Co., with benzene as an eluant, and the benzene eluant was collected. The chromatography was repeated in the same manner as described above and 31 g of Compound (1) was obtained.

SYNTHESIS EXAMPLE 2

Synthesis of Compound (9)

A mixture of 30 g of N-(2-acetyl-2-benzenesulfonylvinyl)aniline, 30 g of 1-decyl-2-methylpyrrolidinium bromide and 300 ml of acetonitrile, was added 10 ml of triethylamine and 20 ml of acetic anhydride and the mixture was refluxed with stirring for 1 hour. The solvent was removed by distillation under reduced pressure. Then, the residue was chromatographically separated using SiO₂ 60 with benzene as an eluant, and the benzene eluant was collected. The chromatography was repeated in the same manner. 17 g of Compound (9) was obtained.

SYNTHESIS EXAMPLE 3

Synthesis of Compound (8)

10 ml of triethylamine was added to a mixture of 34 g of 2-(2-anilinovinyl)-1-ethylpyrrolidinium iodide, 32 g of ethyl trisulfonylacetate and 500 ml of pyridine. After refluxing for 1 hour, the reaction mixture was poured into 2 l of water. The resultant crystals were collected by filtration and washed with diethyl ether. The crystals were recrystallized from ethanol to obtain 31 g of a colorless compound. Next, to this compound, 100 ml of 2-(2,4-di-tert-amylphenoxy)ethanol and 1 ml of tetrabutoxytitanium (as a catalyst) were added and the mixture was heated at 150° C. for 2 hours. After that, to the reaction solution, 500 ml of n-hexane was added and the resultant precipitate was separated by decantation. To the residue, 100 ml of methanol was added and the mixture was cooled with a dry ice bath to form crystals. The resultant crystals were rapidly collected by filtration and then dissolved in benzene. The benzene solution was chromatographically separated using SiO₂ 60 with benzene as an eluant and was collected. 41 g of Compound (8) as a paste was obtained.

Other ultraviolet light absorbing agents of the present invention can be synthesized with ease by one skilled in the art according to the above-described Synthesis Example (1), (2) or (3) or a method similar thereto, i.e., by condensing a compound represented by the general formula (II):

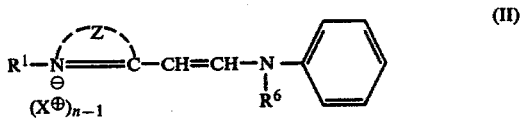

with a compound represented by the general formula (III):

or by condensing a compound represented by the general formula (IV):

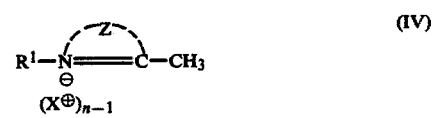

with a compound represented by the general formula (V):

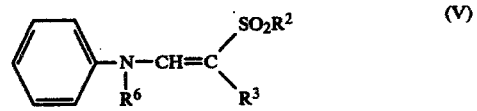

wherein in the general formulae (II) to (V) $R^1$, $R^2$, $R^3$ and Z have the same meaning as defined in the general formula (I); $R^6$ represents a hydrogen atom or an acetyl group; $X^-$ represents an acid anion; and n is 1 or 2 (n being 1 when the compound (II) or (IV) forms an inner salt). Further, the descriptions in U.S. Pat. Nos. 3,486,897 and 3,652,284 may be referred to.

The ultraviolet light absorbing agent of the present invention is superior to known photographic ultraviolet absorbing agents in terms of the absence of deleterious influences upon photographic light-sensitive materials, such as desensitization and coloration due to the following reasons:

(1) The compounds of the present invention have such a high spectral absorption density at about 360 to about 395 nm that a desired absorption density can be obtained using a small amount of the compound, and (2) The compounds of the present invention do not substantially absorb visible light of a wavelength above about 410 nm, particularly above about 420 nm.

The ultraviolet light absorbing agent of the present invention which includes those which are substantially water-insoluble and those which are oils at room temperature can be added to a light-insensitive hydrophilic colloid layer or a light-sensitive silver halide emulsion layer by dissolving them in a water-soluble solvent (e.g., acetone, methyl Cellosolve, methanol and ethanol) and directly dispersing the solution in a coating solution therefor. However, it is preferred for the ultraviolet absorbing agents of the present invention to be added to a light-sensitive silver halide emulsion layer or a light-insensitive hydrophilic colloid layer (e.g., a surface protective layer, an antihalation layer, a subbing layer, a yellow filter layer, an interlayer and a backing layer) by (A) dissolving them in a water-insoluble organic solvent having a high boiling point (hereinafter referred to as an "oil") and emulsifying and dispersing the solution in an aqueous hydrophilic colloid solution (where the ultraviolet absorbing agents are an oil at room temperature, they may be emulsified and dispersed in an aqueous hydrophilic colloid solution in the absence of a solvent), or (B) emulsifying and dispersing them in an aqueous latex in the presence of a substantially water-insoluble auxiliary solvent as described below. In the above-described emulsified dispersion, an auxiliary solvent (e.g., water-soluble solvents such as methanol, acetone and methyl Cellosolve, and substantially water-insoluble solvents such as ethyl acetate and butyl acetate) can be used as described in, for example, U.S. Pat. Nos. 2,739,888 and 3,351,681 and Japanese Patent Application (OPI) No. 59943/1976.

Examples of high boiling point oils which can be used are those having a boiling point of about 140° C. or higher, preferably 170° C. or higher, with specific examples thereof including alkyl phthalates (e.g., dibutyl phthalate and dioctyl phthalate), trimellitic acid esters (e.g., tri-t-octyl trimellitate), aromatic ethers (e.g., di-m-tolyl ether, 1,3-dibutoxybenzene, 1,3-dioctyloxybenzene, 2,4-di-t-amylphenoxyhexane, 2,4-di-nonylphenoxybutane, etc.), phosphoric acid esters (e.g., diphenyl phosphate, triphenyl phosphate, tricresyl phosphate and dioctyl butyl phosphate), citric acid esters (e.g., tributyl acetyl citrate), and alkylamides (e.g., N,N-diethyllaurylamide).

Examples of suitable aqueous hydrophilic colloid solutions include a conventional photographic aqueous hydrophilic colloid solution and additionally an "aqueous latex" in which a polymer is dispersed in the above-described aqueous solution (i.e., an oil-in-water type dispersion).

Gelatin is advantageously used as a hydrophilic colloid, however, other hydrophilic colloids, e.g., proteins such as gelatin derivatives, graft polymers of gelatin and other high molecular weight materials, albumin and casein, cellulose derivatives such as hydroxyethyl cellulose, carboxymethyl cellulose and cellulose sulfates, saccharide derivatives such as sodium alginate and starch derivatives, and a variety of synthetic hydrophilic high molecular weight materials such as homo- or copolymers of polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole or the like can be utilized for this purpose.

Gelatin derivatives which can be used include reaction products of gelatin with a variety of compounds such as acid halides, acid anhydrides, isocyanates, bromoacetic acid, alkanesultones, vinylsulfonamides, maleinimide compounds, polyalkylene oxides and epoxy compounds. Specific examples of these compounds are given in, for example, U.S. Pat. Nos. 2,614,928, 3,132,945, 3,186,846 and 3,312,553, British Pat. Nos. 861,414, 1,033,189 and 1,005,784 and Japanese Patent Publication No. 26845/1967.

The above-described graft polymers of gelatin which can be used include polymers wherein a homo- or copolymer of vinyl type monomers, e.g., acrylic acid, methacrylic acid, derivatives thereof such as the esters and amides thereof, acrylonitrile and styrene is grafted onto the gelatin molecule. It is particularly preferred to utilize a graft polymer of gelatin and a polymer which is compatable therewith to some extent, such as a polymer of acrylic acid, methacrylic acid, acrylamide, methacrylamide, and/or hydroxyalkylmethacrylates. Specific examples of these polymers are described in, for example, U.S. Pat. Nos. 2,763,625, 2,831,767 and 2,956,884.

Representative synthetic hydrophilic high molecular weight materials are described in, for example, West German Patent Application (OLS) No. 2,312,708, U.S. Pat. Nos. 3,620,751 and 3,879,205, and Japanese Patent Publication No. 7561/1978.

Latex polymers which can be used for the above-described purpose can be selected from water-insoluble or water-difficultly-soluble synthetic polymers which are known and used for improvement in the physical properties of a photographic layer. Specific examples of these synthetic polymers which can be used include homo- or copolymers of alkyl(meth)acrylates, alkoxyalkyl(meth)acrylates, glycidyl(meth)acrylates, (meth)acrylamide, vinyl esters (e.g., vinyl acetate), acrylonitrile, olefins and/or styrene and polymers of the above-described monomer(s) and additionally a comonomer such as acrylic acid, methacrylic acid, $\alpha,\beta$-unsaturated dicarboxylic acids, hydroxyalkyl(meth)acrylates, sulfoalkyl(meth)acrylates or styrene sulfonic acid. In addition, polymers can be selected from those as described in Japanese Patent Application (OPI) No. 74538/1974, U.S. Pat. Nos. 2,376,005, 2,739,137, 2,853,457, 3,062,674, 3,411,911, 3,488,708, 3,525,620, 3,607,290, 3,635,715 and 3,645,740, British Pat. Nos. 1,186,699 and 1,307,373. Examples of preferred polymers include alkylacrylate type copolymers (more specifically, e.g., copolymers of ethylacrylate and acrylic acid) and vinyl polymers as described in Japanese Patent Application (OPI) No. 74538/1974.

The amount of the ultraviolet light absorbing agent which can be coated according to the present invention ranges from about 50 to about 1,500 mg/m$^2$ for a positive print paper and from about 5 to about 650 mg/m$^2$ for a negative film.

In addition, a suitable ratio of the ultraviolet light absorbing agent used in the present invention to the oil ranges from 0 ml to about 10 ml, preferably from 0 ml to 4 ml of oil, per gram of the ultraviolet light absorbing agent. An appropriate ratio of the auxiliary solvent to the ultraviolet light absorbing agent which can be used in the present invention is approximately the same as or somewhat more than the ratio of the oil to the ultraviolet light absorbing agent.

The amount of the latex polymer (solid content) used is generally from 0 g to about 10 g, preferably from 0 g to 6 g, per gram of the ultraviolet light absorbing agent.

An oil with the ultraviolet light absorbing agent dissolved therein used in the present invention can be emulsified and dispersed directly into a coating solution. Where an ultraviolet light absorbing agent is incorporated in a coating solution for a color photographic light-sensitive material, preferably an emulsified dispersion wherein the ultraviolet light absorbing agent is dissolved in a polymer of an aqueous latex is incorporated into the coating solution, or alternatively an emulsified dispersion wherein an oil with the ultraviolet light absorbing agent dissolved therein is emulsified and dispersed in an aqueous hydrophilic colloid solution and then is incorporated into the coating solution.

The compounds of the present invention provide excellent effects in a small amount using the above-described addition method, as compared to the use of known ultraviolet light absorbing agents. As a consequence, the compound used in the present invention neither softens the photographic layer nor deteriorates the adhesion between layers of a multilayer photographic light-sensitive material and, additionally, does not cause adhesion between photographic light-sensitive materials to occur. Moreover, an emulsified dispersion of or a water-soluble organic solvent solution containing an ultraviolet light absorbing agent which is used in the present invention is sufficiently stable that neither enlargement of the grains nor deposition of crystals therein occur and the emulsified dispersion or the water-soluble organic solvent solution, even when added to a light-sensitive silver halide photographic emulsion or a light-insensitive hydrophilic colloid solution (e.g., a gelatin sol, etc.), does not render such opaque. In addition, the ultraviolet light absorbing agent used in the present invention is more stable against heat than expected.

Ultraviolet light having wavelengths shorter than about 360 nm can be also effectively absorbed by employing a combination of the ultraviolet light absorbing agent used in the present invention and another photographic ultraviolet light absorbing agent as described in, for example, U.S. Pat. Nos. 3,253,921, 3,707,375, 3,705,805, 3,271,156, 3,754,919 and 3,794,493, British Pat. No. 1,338,265, Japanese Patent Publication No. 25337/1975, U.S. Pat. Nos. 3,692,525, 3,738,837 and 3,698,907, Japanese Patent Publications Nos. 26138/1974 and 26139/1974, U.S. Pat. Nos. 3,936,305, 3,687,671 and 3,694,211, a photographic antioxidant (e.g., a hydroquinone derivative, a catechol derivative, an aminophenol derivative, a gallic acid derivative, etc.), a color image-forming agent (e.g., a photographic yellow coupler, etc.) or the like.

The ultraviolet light absorbing agent used in the present invention is most effective when incorporated into photographic layers such as a surface protective layer, a back layer and an antihalation layer, and, with regard to a color photographic light-sensitive material, the above-mentioned layers and additionally an uppermost light-sensitive silver halide emulsion layer and an interlayer.

Silver bromide, silver chloride, silver iodobromide, silver chlorobromide or silver chloroiodobromide, etc., may be used as the silver halide for the silver halide emulsion of the photographic material of this invention. The silver halide emulsion can be produced using any known process. The silver halide emulsion may be a surface latent image type emulsion or an internal latent image type emulsion.

The silver halide emulsion may be sensitized using a chemical sensitizing agent (for example, a sulfur sensitizing agent such as thiourea, allylthiocarbamide, allylisothiocyanate or cystine, etc.; a gold compound such as potassium chloroaurate, auric trichloride or potassium auric thiocyanate, etc.; and many other noble metal sensitizing agents; and many known reduction sensitizing agents, etc.).

Further, a known stabilizing agent or antifogging agent such as triazoles, imidazoles or azaindenes may be added to the silver halide emulsion, if desired.

Moreover, various color image forming compounds can be used for the photographic light-sensitive materials of the present invention. Examples thereof include benzoylacetoanilide type and pivaloylacetoanilide type 2-equivalent or 4-equivalent yellow couplers; pyrazolone type, indazolone type or cyanoacetyl type 2-equivalent or 4-equivalent magenta couplers; phenol type or naphthol type 2-equivalent or 4-equivalent cyan couplers; and cyan or magenta colored couplers (the above-described 2-equivalent yellow, magenta or cyan couplers may be a development inhibitor releasing (DIR) coupler, if desired). These couplers are preferably diffusion resistant. Further, a redox compound which releases a diffusible dye, a coupler which releases a diffusible dye or a dye developer, etc., may be used.

In addition, conventional photographic additives (for example, spectral sensitizing agents, color stain preventing agents, color fade preventing agents, hardening agents, surface active agents or antistatic agents, etc.) may be added, if desired. These compounds are described in, for example, U.S. Pat. No. 3,996,055, column 32 line 23 to column 37 line 25, U.S. Pat. No. 3,994,729, column 2 line 15 to column 5 line 61 and U.S. Pat. No. 3,997,348, column 6 line 51 to column 31 line 9.

Examples of silver halide photographic light-sensitive materials to which the present invention is applicable include black-and-white camera-type high speed films, microfilms, photographic films for the graphic arts (e.g., lithographic films, etc.), color negative films, color reversal films, color direct positive films, color positive films, color papers, or diffusion transfer color light-sensitive materials, etc.

The silver halide light-sensitive materials of the present invention can be processed using any conventional development processing. For example, the process described in *Journal of the Society of Motion Picture and Television Engineers*, Vol. 61, pages 667 to 701, (1953), can be used.

With the silver halide photographic light-sensitive material of the present invention, there is no fog due to the generation of static charges which are formed during production or storage of the light-sensitive materials and additionally an image having a good sharpness by effectively preventing exposure with ultraviolet light can be obtained. Particularly, with the silver halide color photographic light-sensitive material of the present invention, there are no variations in color reproduction due to differences in the ultraviolet light absorption of the camera lens used, so that a color image having improved color reproduction can be obtained.

Further, the color photographic light-sensitive material has advantages such as a reduction in both light fading and light discoloration of the dye image formed. In addition to the above-described advantages, both photographic properties and physical properties such as sensitivity, fog and adhesion are not adversely affected.

The following examples are given to explain the present invention in greater detail.

EXAMPLE 1

To a mixture (1) of 1,000 g of a 10% aqueous gelatin solution and 75 ml of a 5% sodium dodecylbenzenesulfonate aqueous solution at a temperature of 50° C., a mixture (2) of 40 ml of dibutyl phthalate, 100 ml of ethyl acetate and 20 ml of a 20% solution of sorbitan monolaurate in methanol was added at 50° C. and emulsified and dispersed using a high speed stirring type colloid mill for 5 minutes to produce Emulsified Dispersion A, which was used as a control.

Subsequently, a mixture (3) wherein 80 g of Compound (1) as described above was dissolved in mixture (2) was emulsified and dispersed in mixture (1) to produce Emulsified Dispersion B.

Similarly, Emulsified Dispersion C containing 80 g of Compound (8), Emulsified Dispersion D containing both 20 g of 2-(2-hydroxy-5-tert-butyl)phenylbenzotriazole and 80 g of Compound (1), Emulsified Dispersion F containing 120 g of 2-(2-hydroxy-5-tert-butyl)-phenylbenzotriazole and Emulsified Dispersion G containing 120 g of n-decyl 4-methoxy-α-cyanocinnamate were prepared.

Separately, 1,000 g of an aqueous latex (solid concentration: 10 weight %) containing a copolymer of ethyl acrylate and acrylic acid with a monomer molar ratio of 95:5 was mixed with mixture (1) and into the resultant mixture, the same solution as mixture (3) except the dibutyl phthalate was not employed was emulsified and dispersed to produce Emulsified Dispersion E.

The following layers were then applied to a support to produce samples.

FIRST LAYER

An antihalation layer containing the following dyes fixed with a mordant as illustrated below.

| | Amount Coated |
|---|---|
| Cyan Dye [structure] | about 200 mg/m² |
| Magenta Dye [structure] | about 200 mg/m² |
| Yellow Dye [structure] | about 200 mg/m² |
| Mordant [structure] (x:y = 77:23 molar ratio) | 0.5 g/g binder |

SECOND LAYER

A red-sensitive silver iodobromide (AgI: 4 mol%) gelatin emulsion layer containing oil-soluble diffusion resistant cyan couplers Cyan Couplers (a) [structure with OH, CONH(CH$_2$)$_3$O—, C$_5$H$_{11}$-(t)]

and (b) [structure with OH, CONH—naphthyl, N=N—, COOCH$_2$CHC$_8$H$_{17}$, C$_6$H$_{13}$]

(a:b = 5:1 weight ratio)

(molar ratio of silver/coupler: 25:1, amount of silver coated: 30 mg/100 cm²).

THIRD LAYER

An intermediate layer containing gelatin.

FOURTH LAYER

A green-sensitive silver iodobromide (AgI: 3.5 mol%) gelatin emulsion layer containing diffusion resistant magenta couplers Magenta Couplers (a)

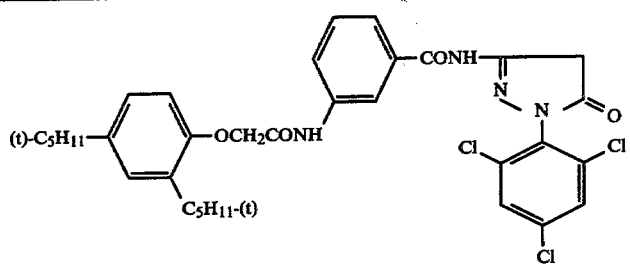

and
(b)

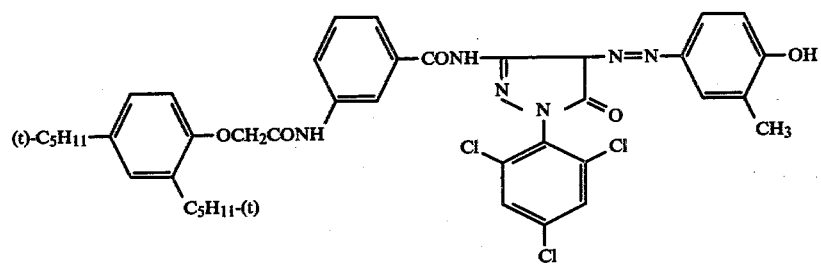

(a:b = 1:1 weight ratio)

(molar ratio of silver/coupler: 35:1, amount of silver coated: 20 mg/100 cm²).

FIFTH LAYER

A gelatin layer having a yellow filter function (the same yellow dye as that of the First Layer was used; amount of dye coated: 300 mg/m².

SIXTH LAYER

A silver iodobromide (AgI: 3 mol%) gelatin emulsion containing a diffusion resistant yellow coupler Yellow Coupler

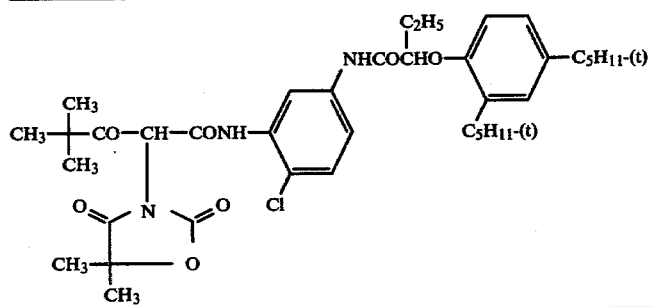

(molar ratio of silver/coupler: 10:1; amount of silver coated: 20 mg/100 cm²).

SEVENTH LAYER

A layer of the above-described Emulsified Dispersion A coated in an amount of 1.50 g/m².

This material was designated Sample 1.

Similarly, Sample 2, Sample 3, Sample 4, Sample 5, Sample 6 and Sample 7 were produced using Emulsified Dispersion B, Emulsified Dispersion C, Emulsified Dispersion D, Emulsified Dispersion E, Emulsified Dispersion F and Emulsified Dispersion G, respectively, instead of Emulsified Dispersion A. The emulsified dispersions are summarized in the Table 1 below.

Table 1

| Component | Emulsified Dispersion | | | | | | |
|---|---|---|---|---|---|---|---|
| | A | B | C | D | E | F | G |
| Gelatin (19% aqueous solution | 1000 g | 1000 g | 1000 g | 1000 g | 1000 g | 1000 g | 1000 g |
| Sodium Dodecylbenzenesulfonate (5% aqueous solution | 75 ml | 75 ml | 75 ml | 75 ml | 75 ml | 75 ml | 75 ml |
| Ethylacrylate-Acrylic Acid Copolymer Latex (10% aqueous solution) | — | — | — | — | 1000 g | — | — |

Table 1-continued

| Component | Emulsified Dispersion | | | | | | |
|---|---|---|---|---|---|---|---|
| | A | B | C | D | E | F | G |
| Dibutyl Phthalate | 40 ml | 40 ml | 40 ml | 40 ml | 40 ml | 40 ml | 40 ml |
| Ethyl Acetate | 100 ml | 100 ml | 100 ml | 100 ml | 100 ml | 100 ml | 100 ml |
| Sorbitan Monolaurate | 20 ml | 20 ml | 20 ml | 20 ml | 20 ml | 20 ml | 20 ml |
| Compound (1) | — | 80 g | — | 80 g | 80 g | — | — |
| Compound (8) | — | — | 80 g | — | — | — | — |
| 2-(2-Hydroxy-5-tert-butyl)phenylbenzotriazole | — | — | — | 20 g | — | 120 g | — |
| n-Decyl 4-Methoxy-α-cyanocinnamate (for comparison) | — | — | — | — | — | — | 120 g |

In order to measure variations in the color balance of the photographic light-sensitive materials caused by use of different kinds of camera lenses wherein the percent transmission of ultraviolet light differed from lens to lens, a gray chart was photographed (exposure: about 10,000 lux for 1/250 second) using a camera equipped with a lens of a high percent transmission of ultraviolet light and a camera equipped with the same lens as described above but having a filter which cut light of wavelengths below 390 nm. After exposure, the samples were processed.

| Process | Temperature (°C.) | Time |
|---|---|---|
| Color Development | 38 | 3 min and 15 sec |
| Bleaching | 38 | 6 min and 30 sec |
| Water Wash | 38 | 3 min and 15 sec |
| Fixing | 38 | 6 min and 30 sec |
| Water Wash | 38 | 3 min and 15 sec |
| Stabilizing | 38 | 1 min and 30 sec |

The processing solutions used had the following compositions.

| Color Developer Solution: | |
|---|---|
| Water | 800 ml |
| Potassium Carbonate (anhydrous) | 38 g |
| Sodium sulfite (anhydrous) | 4 g |
| Sodium Bromide | 1.5 g |
| Hydroxylamine Sulfate | 2.5 g |
| EDTA | 2.5 g |
| 4-[N-Ethyl-N-(β-ethoxyethyl)amino]-2-methylaniline Sulfate | 4.7 g |
| Water to make | 1 l |
| | (pH 10.0) |

| Bleaching Solution: | |
|---|---|
| Water | 600 ml |
| Ammonium Bromide | 150 g |
| Edta-Fe(III) Sodium Salt | 100 g |
| Glacial Acetic Acid | 10 ml |
| EDTA | 10 g |
| Water to make | 1 l |

| Fixing Solution: | (pH 6.0) |
|---|---|
| Water | 800 ml |
| Ammonium Thiosulfate (70% aq. soln.) | 140 ml |
| Sodium Bisulfite (anhydrous) | 12 g |
| Water to make | 1 l |

| Stabilizing Solution: | |
|---|---|
| Water | 800 ml |
| Formaldehyde (37% aq. soln.) | 5.0 ml |
| Polyethylene Glycol | 0.2 g |
| Ethylene Glycol | 2 g |
| Water to make | 1 l |

The resultant negative images in both cases were then evaluated by measuring the red light density, the green light density and the blue light density in both cases. The difference in the densities under each type of light are shown in Table 2 below.

Table 2

| Density* Difference | Sample | | | | | | |
|---|---|---|---|---|---|---|---|
| | (1) | (2) | (3) | (4) | (5) | (6) | (7) |
| Red | 0 | 0 | 0 | 0 | 0 | 0 | 0 |
| Green | 0 | 0 | 0 | 0 | 0 | 0 | 0 |
| Blue | 0.15 | 0.04 | 0.03 | 0.03 | 0.02 | 0.13 | 0.12 |

*The values in Table 2 represent the difference between the image density in the case of photographing using a lens through which ultraviolet light completely passed and the image density in the case of photographing using the same lens equipped with a filter which cuts light below 390 nm (the density is the red light density, the green light density and the blue light density, respectively).

It can be understood from the results in Table 2 above that variations in the blue density were less in the photographic light-sensitive materials of the present invention containing Compounds (1) and (8) (Samples 2 to 5) in a small amount, that the photographic light-sensitive materials are less affected by variations in the percent transmission of ultraviolet light and that the gray balance was excellent.

The use of colloidal silver in place of the dyes in the above-described antihalation layer and filter layer also provided the same results as described above (4 mg of silver per 100 cm$^2$ of the antihalation layer and 1 mg of silver per 100 cm$^2$ of the filter layer).

In addition, where the Fifth Layer is a gelatin layer without a yellow filter function, a similar result was obtained.

Furthermore, the use of Compound (16) also provided an excellent effect equivalent to those which were obtained by employing Compounds (1) and (8).

EXAMPLE 2

The First Layer, the Second Layer, the Third Layer, the Fourth Layer and the Fifth Layer as described in Example 1 were provided in the same manner on a support as described in Example 1, and the Sixth Layer was produced as described below using emulsified dispersions described in Example 1. A protective layer of gelatin was coated on the Sixth Layer. In order to form the Sixth Layer, Emulsified Dispersion F was incorporated in an amount of 1.93 g/m² in the silver iodobromide emulsion and the blue-sensitive layer was coated to produce Sample 7. Emulsified Dispersion F in Sample 7 was replaced with Emulsified Dispersion G to produce Sample (II), Emulsified Dispersion F in Sample 7 with Emulsified Dispersion B to produce Sample (III), Emulsified Dispersion F in Sample 7 with Emulsified Dispersion C to produce Sample (IV) and Emulsified Dispersion F in Sample 7 with Emulsified Dispersion D to produce Sample (V). These samples were exposed, processed and evaluated in the same manner as described in Example 1. The results obtained are shown in Table 3 below.

Table 3

| Density Difference | Sample | | | | |
|---|---|---|---|---|---|
| | I* | II* | III | IV | V |
| Red | 0 | 0 | 0 | 0 | 0 |
| Green | 0 | 0 | 0 | 0 | 0 |
| Blue | 0.14 | 0.13 | 0.06 | 0.05 | 0.05 |

*Comparison (The density difference in Table 3 has the same meaning as in Example 1.)

It can be understood from the results shown in Table 3 above that the compounds of the present invention have the effect of cutting ultraviolet light and reducing variations in the color balance caused by differences in camera lenses, even though they are added to the blue-sensitive layer.

EXAMPLE 3

Samples 1, 2, 3, 4, 5, 6 and 7 prepared as described in Example 1 were evaluated to determine the generation of static charges.

The protective layer of Samples 1, 2, 3, 4, 5, 6 and 7 was rubbed fifty times back and forth in a dark room with a rubber roll positioned in the triboelectric series at substantially 0 voltage to cause light emission by discharging. These samples were developed in the same manner as in Example 1 and the degree of static marks formed in each sample was measured. The increase in maximum density due to static marks was as shown in Table 4 below.

Table 4

| Density Difference | Sample | | | | | | |
|---|---|---|---|---|---|---|---|
| | (1)* | (2) | (3) | (4) | (5) | (6) | (7) |
| Red Density | 0 | 0 | 0 | 0 | 0 | 0 | 0 |
| Green Density | 0 | 0 | 0 | 0 | 0 | 0 | 0 |
| Blue Density | 1.05 | 0.20 | 0.15 | 0.10 | 0.10 | 0.80 | 0.65 |

*Control

It is clear from the results in Table 4 that the occurrence of static marks was reduced by the addition of the compounds of the present invention.

(The Red Density, Green Density and Blue Density in Table 4 each means the image density measured under a red, green or blue light.)

EXAMPLE 4

10 g of Compound (7) of the present invention as an ultraviolet light absorbing agent was dissolved in a mixture of 5 ml of tricresyl phosphate and 10 ml of ethyl acetate, and the resultant solution was emulsified and dispersed in 100 g of a 10% gelatin aqueous solution containing sodium dodecylbenzenesulfonate. The emulsified dispersion thus-prepared was mixed with 200 g of a 10% aqueous solution of gelatin and then coated as the Fourth Layer of the multilayer photographic light-sensitive material as illustrated in Table 5 below. The thus-produced light-sensitive material was designated Sample (a).

Additionally, 10 g of 2-(2-hydroxy-5-tert-butyl)-phenylbenzotriazole for comparison was emulsified and dispersed in the same manner as described above, and the resultant dispersion was mixed with 20 g of a 10% gelatin aqueous solution. Similarly, this mixture was applied to the Fourth Layer of the multilayer photographic light-sensitive material described in Table 5 below. The thus-produced material was designated Sample (b).

The amount of the ultraviolet light absorbing agent, gelatin and tricresyl phosphate each coated in the Fourth Layer is shown in Table 6 below.

Sample (c) was the same as Sample (a) except that the Fourth Layer therein contained no ultraviolet light absorbing agent.

Table 5

Sixth Layer
Gelatin
(coated amount: 1,000 mg/m²)
Fifth Layer
Red-sensitive layer containing silver chlorobromide emulsion
(Br: 50 mol%, coated amount: 300 mg of Ag/m²)
Cyan coupler:
2-[α-(2,4-Di-t-amylphenoxy)butanamido]-4,6-dichloro-5-methylphenol(coated amount: 400 mg/m²)
Gelatin
(coated amont: 1,000 mg/m²)
Coupler solvent:
Dibutyl phthalate (coated amount: 200 mg/m²)
Fourth Layer (see also Table 6)
Intermediate layer containing gelatin
(coated amount: 1,200 mg/m²)
Third Layer
Green-sensitive layer containing silver chlorobromide emulsion
(Br: 50 mol%, coated amount: 400 mg of Ag/²)
Magenta coupler:
1-(2,4,6-Trichlorophenyl)-3-[(2-chloro-5-tetradecanamido)anilino]-5-pyrazolone (coated amount: 300 mg/m²)
Gelatin
(coated amount: 1,000 mg/m²)
Coupler solvent:
Tricresyl phosphate (coated amount: 300 mg/m²)
Dioctylhydroquinone (coated amount: 60 mg/m²)
Second Layer
Intermediate layer containing gelatin
(coated amount: 1,000 mg/m²)
First Layer
Blue-sensitive layer containing silver chlorobromide emulsion
(Br: 80 mol%, coated amount: 400 mg of Ag/m²)
Yellow coupler:
α-Pivaloyl-α-(2,4-dioxo-5,5'-dimethyloxazolidin-3-yl)-2-chloro-5-[α-(2,4-di-t-amylphenoxy)butanamido]-acetanilide (coated amount: 300 mg/m²)
Gelatin
(coated amount: 1,200 mg/m²)
Coupler solvent:
Dibutyl phthalate (coated amount: 150 mg/m²)

Table 6

| | Amount Coated for Fourth layer (mg/m²) | | |
|---|---|---|---|
| | Sample | | |
| Additive | (a) | (b) | (c) |
| Ultraviolet Light Absorbing Agent | 400 | 1,000 | 0 |
| Tricresyl Phosphate | 400 | 500 | 0 |
| Gelatin | 1,200 | 1,200 | 1,200 |

These samples were exposed with light from an iodine lamp through a green filter for 1 second at 1,000 lux using a continuous wedge and then processed as described below with processing solutions having the following composition.

| Processing Steps | Temperature | Time |
|---|---|---|
| Developing Solution | 33° C. | 3 min and 30 sec |
| Bleach-Fixing | 33° C. | 1 min and 30 sec |
| Washing | 28° C.–35° C. | 3 min |

| Developing Solution | |
|---|---|
| Benzyl Alcohol | 15 ml |
| $Na_2SO_3$ | 5 g |
| KBr | 0.4 g |
| Hydroxylamine Sulfate | 2.0 g |
| 4-Amino-3-methyl-N-ethyl-N-$\beta$-(methanesulfonamido) ethylaniline | 10.0 g |
| $Na_2CO_3$ | 30.0 g |
| Diethylenetriamine Pentaacetic Acid | 5.0 g |
| Water to make | 1,000 ml (pH 10.1) |

| Bleach-Fixing Solution | |
|---|---|
| Ammonium Thiosulfate (70% aq. soln.) | 150 ml |
| $Na_2SO_3$ | 5 g |
| Na[Fe(EDTA)] | 40 g |
| EDTA | 4 g |
| Water to make | 1,000 ml (pH 6.8) |

Fading of the dye images formed in the samples was evaluated with a fluorescent fademeter (20,000 lux) for 2 weeks.

The results obtained are shown in Table 7 below.

Table 7

| | Difference in Density after Fading Testing | |
|---|---|---|
| Sample | Yellow Density due to Fog Formation | Density 2.0 (magenta density) |
| (a)* | +0.05 | −0.60 |
| (b)** | +0.05 | −0.65 |
| (c)** | +0.05 | −0.80 |

*Present Invention
**Comparison

The fog is due to light discoloration and is shown by the yellow density measured.

As is apparent from the results in Tables 6 and 7 above, Sample (a) containing the ultraviolet light absorbing agent of the present invention provides the same or more effective results as compared to that of Sample (b), even though the amount of the Fourth Layer coated of Sample (a) was 1/2.5 times that of Sample (b).

EXAMPLE 5

10 g of 2-[α-(2,4-di-t-amylphenoxy)butanamido]-4,6-dichloro-5-methylphenol and 2 g of Compound (7) of the present invention were dissolved in 5 ml of tricresyl phosphate. The resultant solution was emulsified and dispersed in 80 g of a 10% aqueous gelatin solution containing sodium dodecylbenzene-sulfonate.

After that, the thus-obtained emulsified dispersion was added to 145 g of a red-sensitive silver chlorobromide emulsion (50 mol% of Br, 7.5 g of silver), and then the emulsion was coated onto a paper support laminated with polyethylene to produce Sample (d).

Similarly, for comparison, the same cyan coupler emulsified dispersions were prepared as described above except that 2-(2-hydroxy-5-tert-butyl)phenylbenzotriazole was employed as an ultraviolet light absorbing agent in place of the Compound (7) in an amount of 6 g which was 3 times that of Compound (7), and except for the absence of the ultraviolet light absorbing agent, respectively. These comparable emulsified dispersions were then mixed with red-sensitive silver chlorobromide emulsions in the same manner as described above to produce Samples (e) and (f), respectively.

These Samples (d), (e) and (f) were each exposed with light from an iodine lamp to light through a red filter using a continuous wedge for 1 second at 1,000 lux and were subjected to development processing in the same manner as described in Example 1. Subsequently, the fading of the cyan dye image formed in each of these samples was evaluated (for 2 days) using a xenon fademeter.

The change in density at an initial cyan density of 2.0 after fading is given in Table 8 below.

Table 8

| Sample | Change in Density |
|---|---|
| (d)* | −0.30 |
| (e)** | −0.30 |
| (f)** | −0.50 |

*Present Invention
**Comparison

It can be understood from the results shown in Table 8 that the ultraviolet light absorbing agent used in the present invention has an advantage in providing the same effect as that of a hitherto known ultraviolet light absorbing agent but used in an amount of ⅓ times that of the known ultraviolet absorbing agent.

While the invention has been described in detail and with reference to specific embodiments thereof, it will be apparent to one skilled in the art that various changes and modifications can be made therein without departing from the spirit and scope thereof.

What is claimed is:

1. A light-sensitive silver halide photographic element comprising a support having thereon at least one light-sensitive silver halide emulsion layer, wherein said silver halide photographic element comprises, in at least one layer coated thereon, which may be said light-sensitive emulsion layer, at least one water-insoluble compound represented by the following general formula (I):

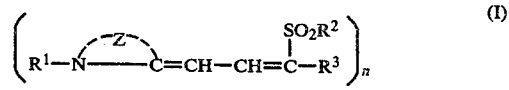

wherein Z represents the atoms necessary to complete an oxazolidine ringe, a pyrrolidine ring or a thiazolidine ring; $R^1$ and $R^2$, which may be the same or different, each represents an alkyl group or an aryl group; $R^3$ represents a —$COR^4$ group or a —$CO_2R^5$ group; $R^4$ represents an alkyl group or an aryl group; $R^5$ represents a hydrogen atom, an alkyl group or an aryl group; and n is 1 or 2 and when n is 2, at least one of $R^1$, $R^4$ and $R^5$ represents a divalent alkylene group, a divalent arylene group or a divalent group of alkylene and arylene moieties to form a dimer, wherein if the photographic element is a positive film or layer the at least one compound of general formula I(I) is present in an amount of about 50 to about 1,500 mg/m² and
  if the photographic element is a negative film the at least one compound of general formula (I) is present in an amount of about 5 to about 650 mg/m².

2. The photographic element of claim 1, wherein the silver halide photographic element contains a substantially light-insensitive hydrophilic colloid layer and the compound represented by the general formula (I) is present as an emulsified dispersion in the light-sensitive silver halide emulsion layer and/or in a substantially light-insensitive hydrophilic colloid layer of said element.

3. The photographic element of claim 2, wherein the compound represented by the general formula (I) is present in the light-sensitive silver halide photographic emulsion layer and/or a substantially light-insensitive hydrophilic colloid of the element layer in the form of a dispersion of oil droplets of said compound represented by the general formula (I) dissolved in a water-insoluble organic solvent having a high boiling point or in the form of latex polymer particles containing said compound represented by the general formula (I).

4. The photographic element of claim 1, wherein at least one of $R^1$, $R^2$, $R^4$ and $R^5$ is an unsubstituted alkyl group or an alkyl group substituted with one or more of a hydroxy group, a halogen atom, an aryl group, an alkoxycarbonyl group, an alkoxy group, an alkylcarbonyl group, an arylcarbonyl group, an alkylcarbonyloxy group, an arylcarbonyloxy group, an alkylsulfonyl group, a morpholinocarbonyl group, a carbamoyl group, an N,N-dialkylcarbamoyl group, an N-alkyl-N-arylcarbamoyl group, an N-alkylcarbamoyl group, an N,N-dialkylamino group and an aryloxy group.

5. The photographic element of claim 1, wherein the compound represented by the general formula (I) is hydrophobic.

6. The photographic element of claim 1, wherein the compound of the general formula (I) is a solid having a boiling point of about 150° C. or less or is a liquid at room temperature.

7. The photographic element of claim 1, wherein the compound of the general formula (I) is a solid having a boiling point of 100° C. or less.

8. The photographic element of claim 1, wherein the photographic material is a positive film or a paper.

9. The photographic element of claim 1, wherein the photographic material is a negative film.

10. A method of preventing the effects of ultraviolet light on a light-sensitive silver halide photographic element comprising a support having thereon at least one light-sensitive silver halide emulsion layer and/or on an image obtained by photographically processing said photographic element after image-wise exposure, which comprises incorporating, as an ultraviolet light absorbent, into at least one layer of said silver halide photographic element an emulsified dispersion of at least one water-insoluble compound represented by the following general formula (I):

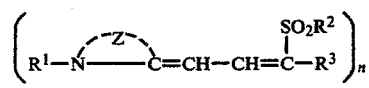

wherein Z represents the atoms necessary to complete an oxazolidine ring, a pyrrolidine ring or a thiazolidine ring; $R^1$ and $R^2$, which may be the same or different, each represents an alkyl group or an aryl group; $R^3$ represents a —$COR^4$ group or a —$CO_2R^5$ group; $R^4$ represents an alkyl group or an aryl group; $R^5$ represents a hydrogen atom, an alkyl group or an aryl group; n represents 1 or 2, and when n is 2, at least one of $R^1$, $R^4$ and $R^5$ represents a divalent alkylene group, a divalent arylene group or a divalent group of alkylene and arylene moieties to form a dimer,
  wherein if the photographic element is a positive film or layer the at least one compound of general formula (I) is present in an amount of about 50 to about 1,500 mg/m² and
  if the photographic element is a negative film the at least one compound of general formula (I) is present in an amount of about 5 to about 650 mg/m².

11. The method of claim 10, wherein the silver halide photographic element comprises a substantially light-insensitive hydrophilic colloid layer and the compound represented by the general formula (I) is incorporated as an emulsified dispersion in the light-sensitive silver halide emulsion layer and/or in the substantially light-insensitive hydrophilic colloid layer.

12. The method of claim 11, wherein the compound represented by the general formula (I) is incorporated in the light-sensitive silver halide photographic emulsion layer and/or the substantially light-insensitive hydrophilic colloid layer in the form of a dispersion of oil droplets of said compound represented by the general formula (I) dissolved in a water-insoluble organic solvent having a high boiling point or in the form of latex polymer particles containing said compound represented by the general formula (I).

13. The method of claim 10, wherein at least one of $R^1$, $R^2$, $R^4$ and $R^5$ is an unsubstituted alkyl group or an alkyl group substituted with one or more of a hydroxy group, a halogen atom, an aryl group, an alkoxycarbonyl group, an alkoxy group, an alkylcarbonyl group, an arylcarbonyl group, an alkylcarbonyloxy group, an arylcarbonyloxy group, an alkylsulfonyl group, a morpholinocarbonyl group, a carbamoyl group, an N,N-dialkylcarbamoyl group, an N-alkyl-N-arylcarbamoyl group, an N-alkylcarbamoyl group, an N,N-dialkylamino group and an aryloxy group.

14. The method of claim 10, wherein the compound represented by the general formula (I) is hydrophobic.

15. The method of claim 10, wherein the compound of the general formula (I) is a solid having a boiling point of about 150° C. or less or is a liquid at room temperature.

16. The method of claim 10, wherein the compound of the general formula (I) is a solid having a boiling point of 100° C. or less.

17. The method of claim 10, wherein the photographic material is a positive film or a paper.

18. The method of claim 10, wherein the photographic material is a negative film.

19. The element of claim 1, wherein said at least one compound of general formula (I) is present in said light-sensitive emulsion layer and/or a substantially light-insensitive hydrophilic colloid layer of said element which is a surface protective layer.

20. The element of claim 1, wherein said at least one compound of general formula (I) is present in said light-sensitive emulsion layer and/or a substantially light-insensitive hydrophilic colloid layer of said element which is an antihalation layer.

21. The element of claim 1, wherein said at least one compound of general formula (I) is present in said light-sensitive emulsion layer and/or a substantially light-insensitive hydrophilic colloid layer of said element which is a subbing layer.

22. The element of claim 1, wherein said at least one compound of general formula (I) is present in said light-sensitive emulsion layer and/or a substantially light-insensitive hydrophilic colloid layer of said element which is a yellow filter layer.

23. The element of claim 1, wherein said at least one compound of general formula (I) is present in said light-sensitive emulsion layer and/or a substantially light-insensitive hydrophilic colloid layer of said element which is an interlayer.

24. The element of claim 19, wherein said at least one compound of general formula (I) is present in said surface protective layer.

25. The element of claim 1, wherein Z represents the atom necessary to complete the oxazolidine ring.

26. The element of claim 1, wherein Z represents the atom necessary to complete the pyrollidine ring.

27. The element of claim 1, wherein Z represents the atom necessary to complete the thiazolidine ring.

28. The element of claim 1, wherein $R^3$ is the —$COR^4$ group.

29. The element of claim 1, wherein $R^3$ is the —$CO_2R^5$ group.

30. The method of claim 10, wherein said at least one compound of general formula (I) is incorporated into said light-sensitive emulsion layer and/or a substantially light-insensitive hydrophilic colloid layer of said element which is a surface protective layer.

31. The method of claim 10, wherein said at least one compound of general formula (I) is incorporated into said light-sensitive emulsion layer and/or a substantially light-insensitive hydrophilic colloid layer of said element which is an anti-halation layer.

32. The method of claim 10, wherein said at least one compound of general formula (I) is incorporated into said light-sensitive emulsion layer and/or a substantially light-insensitive hydrophilic colloid layer of said element which is a subbing layer.

33. The method of claim 10, wherein said at least one compound of general formula (I) is incorporated into said light-sensitive emulsion layer and/or a substantially light-insensitive hydrophilic colloid layer of said element which is a yellow filter layer.

34. The method of claim 10, wherein said at least one compound of general formula (I) is incorporated into said light-sensitive emulsion layer and/or a substantially light-insensitive hydrophilic colloid layer of said element which is an interlayer.

35. The method of claim 10, wherein said at least one compound of general formula (I) is incorporated into said surface protective layer.

36. The method of claim 10, wherein Z represents the atom necessary to complete the oxazolidine ring.

37. The method of claim 10, wherein Z represents the atom necessary to complete the pyrollidine ring.

38. The method of claim 10, wherein Z represents the atom necessary to complete the thiazolidine ring.

39. The method of claim 10, wherein $R^3$ is the —$COR^4$ group.

40. The method of claim 10, wherein $R^3$ is the —$CO_2R^5$ group.

* * * * *